(12) United States Patent
Sanquer et al.

(10) Patent No.: US 9,290,792 B2
(45) Date of Patent: Mar. 22, 2016

(54) METHOD FOR MEASURING CALCINEURIN ACTIVITY

(71) Applicants: UNIVERSITE PARIS DESCARTES, Paris (FR); ASSISTANCE PUBLIQUE HOPITAUX DE PARIS, Paris (FR)

(72) Inventors: Sylvia Sanquer, Sevres (FR); Robert Barouki, Sevres (FR); Laurence Herry, Issy les Moulineaux (FR)

(73) Assignees: UNIVERSITE PARIS DESCARTES, Paris (FR); ASSISTANCE PUBLIQUE HOPITAUX DE PARIS, Paris (FR)

( * ) Notice: Subject to any disclaimer, the term of this patent is extended or adjusted under 35 U.S.C. 154(b) by 27 days.

(21) Appl. No.: 14/381,533

(22) PCT Filed: Feb. 14, 2013

(86) PCT No.: PCT/EP2013/052943
§ 371 (c)(1),
(2) Date: Aug. 27, 2014

(87) PCT Pub. No.: WO2013/127636
PCT Pub. Date: Sep. 6, 2013

(65) Prior Publication Data
US 2015/0050681 A1 Feb. 19, 2015

(30) Foreign Application Priority Data

Feb. 27, 2012 (EP) .................................... 12305231

(51) Int. Cl.
*C12Q 1/42* (2006.01)

(52) U.S. Cl.
CPC .............. *C12Q 1/42* (2013.01); *G01N 2560/00* (2013.01); *G01N 2800/52* (2013.01)

(58) Field of Classification Search
CPC ............. A61K 51/088; A61K 51/1021; C07K 14/525; C07K 16/24; C07K 2317/21; C07K 2317/622; C07K 2317/76; C12Q 1/42; G01N 2560/00; G01N 2800/52
See application file for complete search history.

(56) References Cited

U.S. PATENT DOCUMENTS 8,748,119 B2 * 6/2014 Gooch et al. .................... 435/21

FOREIGN PATENT DOCUMENTS

| WO | WO-03/102133 A2 | 12/2003 |
| WO | WO-2007/058893 A2 | 5/2007 |
| WO | WO-2009/018424 A2 | 2/2009 |
| WO | WO-2011/085176 A2 | 7/2011 |

OTHER PUBLICATIONS

International Preliminary Report on Patentability for International Application No. PCT/EP2013/052943, dated Sep. 2, 2014.
International Search Report and Written Opinion for International Application No. PCT/EP2013/052943, mailed May 16, 2013.
Roberts et al., A fluorimetric method for determination of calcineurin activity, Cell Calcium, 43(5):515-9 (2008).

* cited by examiner

*Primary Examiner* — Debbie K Ware
(74) *Attorney, Agent, or Firm* — Marshall, Gerstein & Borun LLP (57) ABSTRACT

The present invention relates to a method for measuring the activity of calcineurin in a biological sample wherein a kinase inhibitor is present in the assay reaction mix.

9 Claims, 5 Drawing Sheets

METHOD FOR MEASURING CALCINEURIN ACTIVITY

FIELD OF THE INVENTION

The present invention relates to a method for measuring the activity of calcineurin in a biological sample.

BACKGROUND OF THE INVENTION

The standard for the prevention of rejection in transplant patients consists in immunosuppressive regimens including a calcineurin inhibitor such as cyclosporine (CsA) or tacrolimus (TAC). However, the optimal balance between a too strong or a too weak immunosuppression is difficult to achieve following transplantation. An inadequate immunosuppression can provoke a transplant rejection and, on the other hand, an excessive immunosuppression facilitates the development of severe complications such as infections or lymphoproliferative disorders. The usual practice consists, for the physicians, in establishing the treatment with fixed doses, then in adjusting the drug doses according to their blood levels or, even more frequently, according to the occurrence of either an acute rejection or adverse drug event. Unfortunately, this strategy is associated with a frequent failure as illustrated by the fact that 30 to 50% of the patients develop acute rejection after transplantation.

A pharmacodynamic approach, based on the measurement of the effect of the drugs on their cellular targets, has been developed with the aim to reduce the incidence and severity of acute rejection. This pharmacodynamic approach is based on the measurement of the activity of calcineurin (CN), a calcium-calmodulin-dependent phosphatase. CN is part of the family of the serine/threonine phosphatase enzyme including PP1, PP2A, PP2B or calcineurin and PP2C (Ingebritsen & Cohen, 1983).

Current calcineurin assays are generally performed in cell extracts obtained from blood mononuclear cells (PBMC, peripheral blood mononuclear cells) from transplant patients (Fruman et al, 1996; Sanquer et al, 2004; Fukudo et al, 2005). These tests are based on the dephosphorylation of a phosphorylated substrate of calcineurin in the presence of calcium and calmodulin which are essential to the activity of the enzyme (Pallen & Wang, 1983). The addition of okadaic acid at a concentration of 500 nM (that inhibits all the phosphatases except CN) avoids the potential cross-reactivity for the phosphorylated substrate.

An especially preferred substrate is the phosphorylated peptide RII (P-RII), derived from the regulatory subunit of protein kinase A (PKA, Donella-Deana et al, 1994). This peptide is characterized by the following sequence: DLD-VPIPGRFDRRVpSVAAE (SEQ ID No:1).

In the different assays described so far, the P-RII peptide can be labelled or not, and the labelling is either performed with a radioelement (32P) or a fluorophore.

Most methods used for measuring CN phosphatase activity are based on the detection of free phosphate released during the enzymatic reaction. These methods use radiometric measurements in the case of P-RII peptide labelled with 32P (Fruman et al, 1996; Koefoed-Nielsen et al, 2004). They use spectrophotometric measurements in the case of unlabelled R-RII peptide. The latter requires the implementation of a second reaction with green malachite to color the free inorganic phosphate (Sellar et al, 2006).

More specific methods based on the direct measurement of the formation of the dephosphorylated peptide RII (DP-RII) by CN have been developed. These methods were originally based on liquid chromatography coupled with UV detection (Enz et al, 1994; Sanquer et al, 2004). These methods were developed for unlabelled P-RII peptide. More recently, a fluorimetric method was described to measure CN activity by using P-RII peptide labelled with a fluorophore (Roberts et al, 2008).

SUMMARY OF THE INVENTION

The invention stems from the observation that biological samples, such as peripheral blood mononuclear cell extracts, contain a kinase activity which can compete with the phosphatase activity of calcineurin. This kinase activity, which was never reported before in the methods for measuring calcineurin activity of the prior art, should be inhibited in order to obtain more specific results.

Indeed, the inventors have observed that the specificity of the calcineurin activity assay can be significantly increased by adding at least one kinase inhibitor to the reaction mix.

Therefore, the present invention relates to a method for measuring the activity of calcineurin in a biological sample comprising the steps of:

provide a reaction mix comprising a substrate, at least one phosphatase inhibitor and at least one kinase inhibitor;

incubating said biological sample with the reaction mix under conditions suitable for the activity of calcineurin;

measuring the amount of dephosphorylated substrate.

The present invention also relates to a kit for measuring the activity of calcineurin in a biological sample comprising a substrate, at least one phosphatase inhibitor and at least one kinase inhibitor.

Another aspect of the invention relates to the use of kinase inhibitor in a method for measuring the activity of calcineurin.

In yet another aspect, the invention relates to a method for predicting the therapeutic outcome of a transplant patient comprising measuring the activity of calcineurin in a biological sample obtained from said patient as described above.

DETAILED DESCRIPTION OF THE INVENTION

The present invention relates to a method for measuring the activity of calcineurin in a biological sample comprising the steps of:

providing a reaction mix comprising a substrate, at least one phosphatase inhibitor and at least one kinase inhibitor;

incubating said biological sample with the reaction mix under conditions suitable for the activity of calcineurin;

measuring the amount of dephosphorylated substrate.

As used herein, the term "calcineurin", is used interchangeably with "CaN", "phosphatase 2B" or "PP-2B", and refers to the $Ca^{2+}$/calmodulin-dependent Serine/Threonine protein phosphatase. This protein catalyses the removal of a phosphate group from its substrate by hydrolysing phosphoric acid monoesters into a phosphate ion and a molecule with a free hydroxyl group. More specifically, calcineurin removes a phosphate group from a phosphorylated serine residue (phospho-serine, or "pS") or a phosphorylated threonine residue (phospho-threonine, or "pT").

Calcineurin is a heterodimer consisting of a catalytic A subunit (57-61 kDa) and a regulatory subunit B (19 kDa). The catalytic A subunit is composed of four functional domains: the catalytic core with sequence homology to PP-1 and PP-2A; binding sites for both calmodulin and the CaN-regulatory subunit, and C-terminal autoinhibitory domain.

As used herein, the term "substrate" or "calcineurin substrate" refers to a phosphoprotein or phosphopeptide which can be hydrolysed by calcineurin. It therefore refers to a phosphoprotein or phosphopeptide having at least one phosphoserine and/or phosphothreonine residue.

The amino acid residues described herein are preferred to be in the "L" isomeric form. However, residues in the "D" isomeric form can be substituted for any L-amino acid residue, as long as the ability of the substrate to be hydrolysed by calcineurin is retained. NH3 refers to the free amino group present at the amino terminus of a polypeptide. COOH refers to the free carboxy group present at the carboxy terminus of a polypeptide.

In keeping with standard polypeptide nomenclature, J. Biol. Chem., 243:3552-59 (1969), abbreviations for amino acid residues are shown in the following Table of Correspondence:

| One-letter code | Three-letter code | Amino acid |
| --- | --- | --- |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

All amino-acid residue sequences are represented herein by formulae whose left and right orientation is in the conventional direction of amino-terminus to carboxy-terminus.

The term "pX", or "phosphoX", as used herein, refers to a phosphorylated amino acid residue X.

Typically, the substrate according to the invention comprises at least one phosphoserine or phosphothreonine residue.

Preferred substrates according to the invention are calcineurin-specific substrates. In other terms, the substrate according to the invention is typically recognized and hydrolysed by calcineurin more efficiently than by other types of phosphatases.

Typically, the substrate according to the invention can be selected from the group consisting of the phosphopeptides described in Table I of Donella-Deana et al. (Donella-Deana et al., 1994, Eur J Biochem 219, 109-117).

Typically, a preferred substrate is a fragment of the regulatory subunit of cAMP-dependent protein kinase type II (RII).

In a still preferred embodiment, the substrate is DLD-VPIPGRFDRRVpSVAAE (SEQ ID NO:1).

The substrate of the invention can be obtained by any suitable method in the art: it can be a recombinant phosphoprotein or fragment thereof, a purified phosphoprotein or fragment thereof, or a synthetic phosphopeptide.

In one embodiment of the invention, the substrate is a synthetic phosphopeptide.

The substrate according to the invention can be labelled, or unlabelled.

Detection of the dephosphorylation reaction product will then be carried out by different means, according to the type of substrate that was used (see below)

As used herein, the expression "conditions suitable for the activity of calcineurin" has its general meaning in the art and refers to the overall physicochemical conditions in which the dephosphorylation reaction catalyzed by calcineurin takes place.

According to one embodiment, the reaction is carried out at a temperature comprised between 20° C. and 40° C., preferably between 25° C. and 38° C., even more preferably around 30° C., 31° C., 32° C., 33° C., 34° C., 35° C., 36° C. or 37° C.

According to one embodiment, the reaction is carried out for a period of time comprised between 5 minutes and 60 minutes, preferably between 10 and 45 minutes, between 15 and 40 minutes, even more preferably about 30 minutes.

In one embodiment of the invention, the reaction is carried out by incubating the biological sample and the reaction mix at 37° C. for 30 minutes.

Typically, the reaction can be stopped after a predetermined amount of time by placing the reaction tube at +4° C. and addition of trichloroacetic acid (TCA).

According to the invention, the dephosphorylation of the substrate by calcineurin is carried out in a reaction mix. As used herein, the expression "reaction mix" or "assay reaction mix" has its general meaning in the art. In refers to the solution in which the enzymatic reaction to be quantified is carried out. Typically, the assay reaction mix according to the invention is an aqueous solution comprising all the necessary reagents for the enzymatic reaction to take place.

Typically, the reaction mix comprises water, a pH buffer and salts.

Suitable pH buffers according to the invention are phosphate-free buffers, such as Tris-HCl.

Typically, the pH of the reaction mix is comprised between 6.0 and 8.0, preferably around 7.0.

In one embodiment, the reaction buffer comprises $Ca^{2+}$ and calmodulin. Indeed, the phosphatase activity of native calcineurin is dependent on the presence of $Ca^{2+}$ and calmodulin.

Typically, the assay reaction mix can comprise a final concentration of calmodulin comprised between 0.01 and 0.06 units, preferably about 0.03 units.

Typically, the assay reaction mix comprises a final concentration of $Ca^{2+}$ comprised between 30 µM and 90 µM, preferably about 50 µM.

In one embodiment of the invention, protease inhibitors are added to the biological sample and/or to the reaction mix. Indeed, the presence of such inhibitors avoids the degradation of the calcineurin present in the biological sample by endogenous proteases. Suitable protease inhibitors include, but are not limited to PMSF, EDTA, EGTA, aprotinin, leupeptin, pepstatin and mixtures thereof.

The reaction according to the invention is carried out in the presence of at least one phosphatase inhibitor.

As used herein, the expression "phosphatase inhibitor" has its general meaning in the art. It refers to a compound that inhibits at least one phosphatase. Typically, the phosphatase inhibitor according to the invention is not a calcineurin inhibitor at the selected concentration.

Suitable phosphatase inhibitors according to the invention include phosphatase-specific inhibitors and broad spectrum inhibitors.

Typically, the phosphatase inhibitor according to the invention is okadaic acid. Okadaic acid (9,10-Deepithio-9,10-didehydroacanthifolicin) is a potent inhibitor of protein phosphatase 1 (PP-1; IC50=20-100 nM), protein phosphatase 2A (PP-2A; IC50=0.1-1 nM) and protein phosphatase 2B (PP-2B; IC50>5000 nM).

Typically, okadaic acid is used at a final concentration ranging from 100 to 1000 nM, preferably about 500 nM.

Another suitable phosphatase inhibitor is microcystin-LR.

The reaction according to the present invention is carried out in the presence of at least one kinase inhibitor.

Indeed, the inventors have demonstrated, for the first time, that biological samples contained a kinase activity which competes with the calcineurin phosphatase activity, leading to loss of specificity of the previously described assays.

Therefore, carrying out the calcineurin activity assay in the presence of at least one kinase inhibitor leads to improved specificity of the method.

As used herein, the expression "kinase inhibitor" refers to a compound which inhibits the activity of at least one kinase.

According to one embodiment of the invention, the kinase inhibitor is a selective inhibitor of Protein Kinase A (PKA).

It falls within the ability of the skilled person in the art to select appropriate PKA inhibitors.

Suitable selective inhibitors of PKA according to the invention can be 1) structural analogs of cAMP, the Rp-cAMPs family, that are competitive inhibitors of the cAMP-binding site, 2) endogenous inhibitors of the activity of PKA: the protein kinase inhibitor peptide (Murray, 2008) and 3) silencing RNA targeted to at least the two isoforms (α and β) of the catalytic subunit of PKA (Murray, 2008; Dumaz et al, 2003; Rudolph et al, 2007; Monagham et al, 2008). These compounds include, but are not limited to Rp-adenosine-3',5'-cyclic monophosphorothioate (Wang et al, 1991); Rp-8-Bromoadenosine 3',5'-cyclic Monophosphorothioate (Gjertsen et al, 1995); Rp-8-bromo-2'-O-monobutyryladenosine-3',5'-cyclic monophosphorothioate (Ruiz-Velasco et al, 1998); Rp-8-chloroadenosine-3',5'-cyclic monophosphorothioate (Yokozaki et al, 1992); Rp-8-(4-chlorophenylthio)adenosine-3',5'-cyclic monophosphorothioate (Weisskupf et al, 1994); Rp-8-hexylaminoadenosine-3',5'-cyclic monophosphorothioate (Gjertsen et al, 1995); Rp-8-hydroxyadenosine-3',5'-cyclic monophosphorothioate (Gjertsen et al, 1995); Rp-8-PIP-cAMPs (Ogreid et al, 1994); PKA inhibitor fragment 14-22 myristoylated (Zhang et al, 2004); PKA inhibitor fragment 6-22 amide (Glass et al, 1989); PKA inhibitor fragment 5-22 amide (Cheng et al, 1986); cAMP-dependent protein kinase inhibitor fragment 5-24, (Cheng et al, 1986).

It falls within the ability of the skilled person to determine the optimal concentration of the PKA inhibitor in the final reaction mix.

In one embodiment, the PKA inhibitor is Rp-adenosine 3'-5' cyclic monophosphorothioate, which can be purchased from Sigma-Aldrich under reference A165.

Typically, Rp-adenosine 3'-5' cyclic monophosphorothioate, can be used at a final concentration of 10 μM.

According to another embodiment of the invention the kinase inhibitor is a non-selective kinase inhibitor. Suitable non-selective kinase inhibitors include, but are not limited to H89 (Murray, 2008); KT5720 (Murray, 2008); chelerythrine (Freemerman et al, 1996); H7 (Qiu et al, 2010); H8 (Hidaka et al, 1984); protein kinase inhibitor from porcine heart.

Typically, the non-selective kinase inhibitor can be H89, which can be purchased from Sigma-Aldrich under reference B1427.

H89 can be used at a final concentration of 20 μM.

In yet another embodiment, the assay reaction mix comprises several kinase inhibitors.

After the dephosphorylation of the substrate by the calcineurin present in the biological sample has been carried out, the amount of dephosphorylated substrate is quantified, either directly or indirectly. The results can be expressed as an absolute measure (such as pmol/mg protein/min), or in arbitrary units.

This step of "measuring the amount of dephosphorylated substrate" can be performed either indirectly (by measuring the amount of free phosphate released by the reaction) or directly (by measured the dephosphorylated substrate itself).

Any method for measuring the amount of dephosphorylated substrate can be used.

Suitable methods include, but are not limited to:
radiometric measurements in the case of a substrate labelled with 32P (Fruman et al. 1996; Koefoed-Nielsen et al., 2004);
fluorescence measurements in the case of a substrate labelled with a fluorophore (Roberts et al., 2008);
spectrophotometric measurements in the case of unlabelled substrate (Sellar et al., 2006).

In one embodiment, the amount of free phosphate is measured using a colorimetric assay and spectrophotometry (Sellar et al., 2006). For example, the calcineurin cellular activity assay kit commercialized by Calbiochem under catalogue number 207007 relies on the detection of free phosphate based on the malachite green assay.

In the above described detection techniques, it is necessary to physically separate:
either the free phosphate from the unmetabolized phosphorylated substrate, for instance, by dowex cation-exchange resin chromatography columns (see Fruman et al. 1996);
or the dephosphorylated peptide from the unmetabolized phosphorylated substrate, for instance using titanium oxide resins (see Roberts et al., 2008) or using liquid chromatography (see Enz et al, 1994) prior to the measurement step itself.

In another embodiment, the amount of dephosphorylated substrate is measured by liquid chromatography.

Suitable chromatography methods are described for instance in Enz et al. (1994).

This document describes a method for quantifying simultaneously phosphorylated and non-phosphorylated peptides by HPLC coupled with UV detection. The experiments disclosed in this document were carried out using purified calcineurin. Sanquer et al., (2004) also describe a detection method based on HPLC coupled with UV detection for measuring the activity of calcineurin in PBMC samples obtained from transplant patients.

In yet another embodiment, the amount of dephosphorylated substrate is measured by liquid chromatography coupled with tandem mass spectrometry (LC-MS/MS). Advantageously, this detection method further improves the sensitivity and specificity of the assay.

In a preferred embodiment, the step of measuring the amount of dephosphorylated substrate is carried out by liquid chromatography coupled with tandem mass spectrometry (LC-MS/MS) as described in the Examples below.

As used herein, the term "biological sample" refers to any biological sample suspected of containing calcineurin activity.

Typically, the biological sample can be a blood sample, a peripheral blood mononuclear cell (PBMC) sample, a cerebrospinal fluid sample or cellular extracts prepared from cell cultures.

In a preferred embodiment, the biological sample is a PBMC sample.

The biological sample according to the invention can be either freshly obtained or kept at +4° C. or +20° C. prior to analysis.

In a preferred embodiment, the biological sample is used within maximum 7 days from its collection, preferably within 4, 3, 2 or 1 day from collection when kept at +4° C. or within the day of collection when kept at +20° C.

Typically, a "patient" denotes a mammal, such as a rodent, a feline, a canine, and a primate. Preferably, a patient according to the invention is a human.

Typically, a patient according to the invention is an immunosuppressed patient, such as a patient having received an organ or stem-cell transplant.

The present invention also relates to a kit for measuring the activity of calcineurin in a biological sample comprising a substrate, at least one phosphatase inhibitor and at least one kinase inhibitor.

In the kit according to the invention, the substrate, the phosphatase inhibitor and the kinase inhibitor are as described above.

The kit according to the invention can further comprise:
recombinant calcineurin, to be used as positive control;
quality controls
calibrators
assay buffer
a leaflet explaining that the reaction should be carried in the presence of at least one kinase inhibitor for optimal results;
and/or means for detecting the amount of free phosphate released by the reaction, such as malachite green (for detection by spectrophotometry).
and/or an internal standard (for detection by liquid chromatography coupled to mass spectrometry).

Another aspect of the invention relates to the use of kinase inhibitor in a method for measuring the activity of calcineurin.

The method for quantifying calcineurin activity in a biological sample has many applications.

For instance, the method can be used to monitor the activity of calcineurin in a biological sample obtained from a patient who has been administered an immunosuppressive treatment.

Typically, patients receiving an organ transplant are given immunosuppressive treatments such as tacrolimus or cyclosporine.

Thus, the invention also relates to a method for predicting the therapeutic outcome of a transplant patient comprising measuring the activity of calcineurin in a biological sample obtained from said patient as described above.

As used herein, the expression "predicting the therapeutic outcome" encompasses both monitoring the level of calcineurin activity in a biological sample of a given patient over time (in a first and second biological sample obtained at two distinct time points) and comparing the level of calcineurin activity in a biological sample obtained from said patient with a reference value. In one embodiment, the reference value may be a value obtained from a population displaying a similar disease to said patient. Alternatively, the reference value may be a value obtained from a healthy population.

EXAMPLES

Material and Methods

Preparation of Cellular Extracts

PBMCs obtained from either healthy volunteers or transplant patients were resuspended in a buffer containing 50 mM Tris, pH=7.0, 0.1 mM EGTA, 0.05 mM dithiothreitol, 0.1% tween 20, 0.3 mg/mL albumin, 1 mM $MnCl_2$, 1 mM $CaCl_2$ and protease inhibitors. These cellular extracts were sonicated on ice, and centrifuged for 30 minutes at 10.000 g at 4° C. The supernatants corresponding primarily to the cytosolic fractions were recovered and their protein content was determined. These cellular extracts can be stored at −80° C. for later measurement of CN activity.

Preparation of Peptides

Stock solutions of the RII peptide, its phosphorylated form and internal standard (stable isotope-RII peptide) were prepared at a concentration of 0.5 g/L in Hepes buffer and were stored at −40° C. Calibrators were prepared by dilution of the stock solutions in Tris-HCl to yield a final calibration range of 0.16, 0.32, 0.63, 0.95, 1.58, 4.74 and 7.9 µM.

Enzymatic Assay

One to 5 µg of proteins obtained from PBMC, prepared as described above, were used for measuring calcineurin activity in a reaction mixture containing 500 nM okadaic acid, 1 mg/L internal standard, 20 µM H89, 8 mg/L phosphorylated RII peptide and 0.03 units calmodulin in 15 µL 50 mM Tris-HCl, pH=7.0. Enzymatic reaction was carried out at 37° C. for 30 min and then, the reaction tubes were cooled on ice and the enzymatic reaction was stopped by addition of 15 µL of a solution of 5% trichloroacetic acid. After centrifugation for 5 minutes at 12.000 g at 4° C., supernatants were transferred to 200-4 glass inserts into 1.5 mL glass autoinjector vials and kept at 4° C. in autosampler before injection.

Chromatographic Conditions

LC-MS/MS was performed using Agilent 1100 series HPLC system connected to an Applied Biosystems API3000 tandem quadrupole mass spectrometer, operated in the electrospray positive ion mode with selected reaction monitoring (SRM). A 24-µL injection was routinely used, and chromatography was achieved with an Agilent Zorbax 300Extend-C18 3.5-µm particle size, 4.6×100 mm column and 5 µm particle size, 4.6×12.5 mm analytical guard column. The flow rate was 0.2 mL/min. Mobile phase A was 5 mM ammonium acetate and 0.1% formic acid in water and mobile phase B, 5 mM ammonium acetate and 0.1% formic acid in acetonitrile. A programmed mobile-phase gradient was used during the 20 min run: 0 min, 2% B; 10 min, 100% B, 15 min, 100% B; 15.5 min 2% B, 20 min, 2% B. Di-charged ion peptides were selected for both P-RII, DP-RII and internal standard as the most intense ionized peptides after electrospray positive ionization mode. The MS/MS instrument and data collection parameters are shown in Table 1.

TABLE 1a

MS/MS instrument parameters

| | |
|---|---|
| Ion spray voltage (V) | 5500 |
| Entrance potential | 10 |
| Temperature (° C.) | 50 |
| Curtain gas | 10 |
| Nebulizer gas | 8 |
| Collision gas | 4 |
| Q1 resolution | unit |
| Q3 resolution | unit |
| Dwell time (ms) | 300 |
| scan type | SRM |
| Ion spray voltage (V) | 5500 |
| Entrance potential | 10 |
| Temperature (° C.) | 50 |
| Curtain gas | 10 |
| Nebulizer gas | 8 |
| Collision gas | 4 |
| Q1 resolution | unit |
| Q3 resolution | unit |
| Dwell time (ms) | 300 |
| scan type | SRM |

TABLE 1.b

Transitions parameters

| compound | m/z Q1 | m/z Q3 | CE | CXP | DP | FP | retention time |
|---|---|---|---|---|---|---|---|
| P-RII peptide | 732.4 | 201.2 | 70 | 10 | 100 | 400 | 14.5 |
| (substrate) | 732.4 | 70.1 | 90 | 10 | 46 | 320 | |
| DP-RII peptide | 705.8 | 70.1 | 95 | 8 | 51 | 370 | 14.6 |
| (product) | 705.8 | 201.2 | 59 | 20 | 51 | 370 | |
| internal | 708.5 | 70.1 | 89 | 8 | 96 | 370 | 14.6 |
| standard | 708.5 | 201.2 | 55 | 18 | 96 | 370 | |

CE: collision energy (eV) CXP: collision cell exit potential (eV); DP: declustering potential (eV) FP: focusing potential (eV).

Assay Validation

Figure 3:
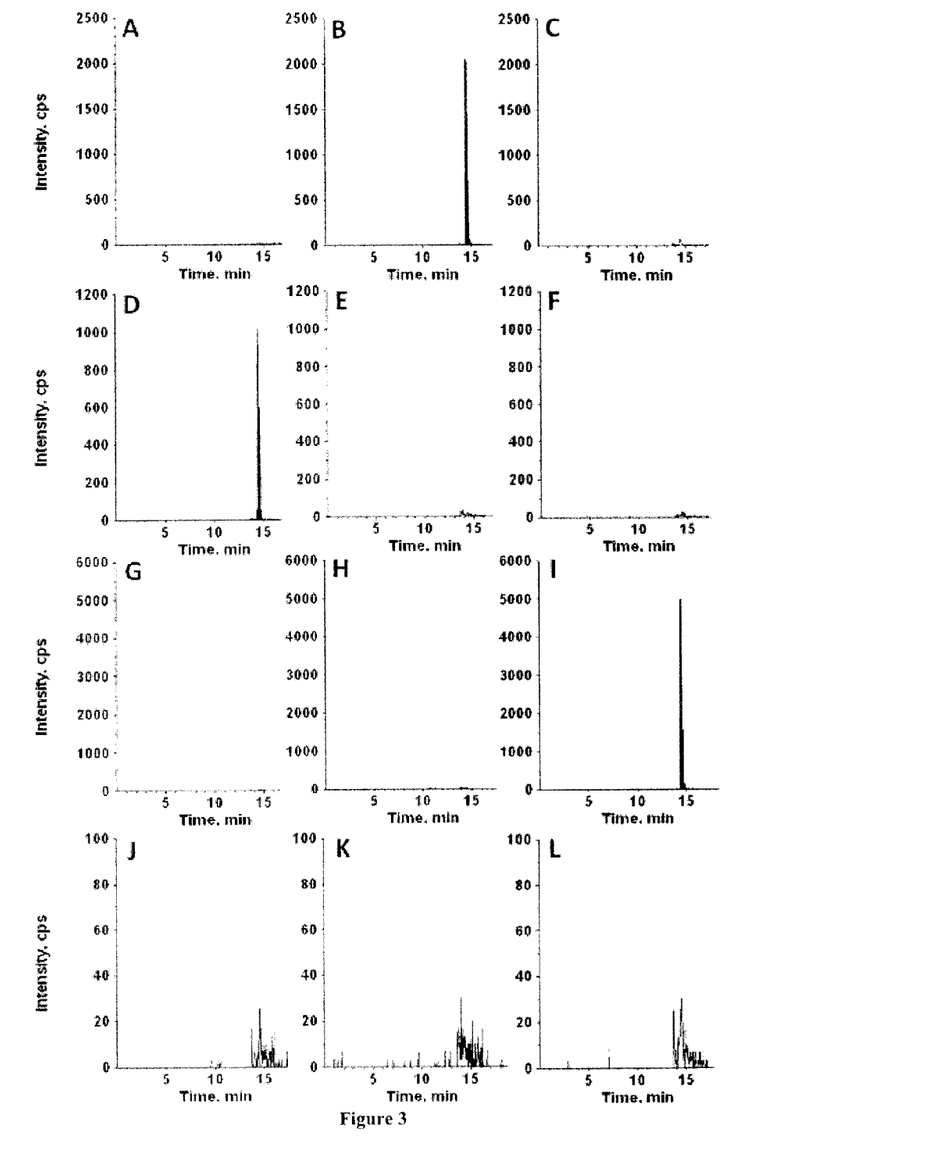
FIG. 3: Chromatographic profiles of P-RII peptide, DP-RII peptide and stable isotope-RII peptide in PBMC protein extract. A,B,C: 1 mg/L RII peptide in PBMC protein extracts; D,E,F: 1 mg/L P-RII in PBMC protein extracts; G,H,I: 1 mg/L stable isotope-RII peptide in PBMC protein extracts; J,K,L: blank PBMC protein extracts; A,D,G,J: transition 732.4>70.1 (P-RII peptide); B,E,H,K: transition 705.8>70.1 (DP-RII peptide); C,F,I,L: transition 708.3>70.1 (stable isotope-RII peptide).

The chromatographic profiles for blank PBMC protein extracts and PBMC protein extracts containing either P-RII peptide, DP-RII peptide or internal standard are shown in FIG. 3. As can be seen in FIG. 3, the selected transitions for each peptide of interest is specific of a given peptide, and none of them are found in blank PBMC protein extracts. Phosphorylated RII peptide had a retention time of 14.5 min and both DP-RII peptide and internal standard had similar retention times of 14.6 min.

Figure 4:
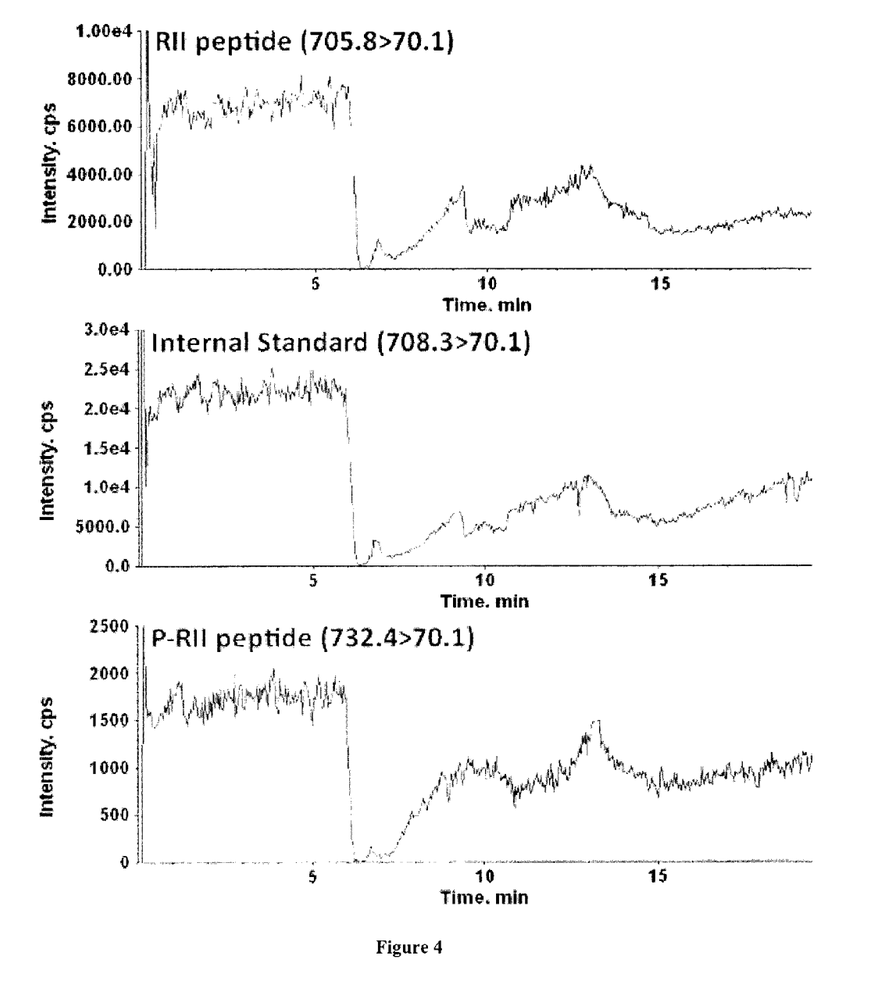
FIG. 4: Ion suppression profiles for postcolumn infusion of PBMC protein extracts.

Representative ion suppression profiles for a PBMC protein extract analyzed by LC-MS/MS are shown in FIG. 4. Suppression effects occurred mainly between 6 and 11 minutes of the chromatography, then the signal stabilized gradually. The small ion suppression effect observed at the elution times of the peptides of interest can be neglected due to co-elution of internal standard.

Figure 5:
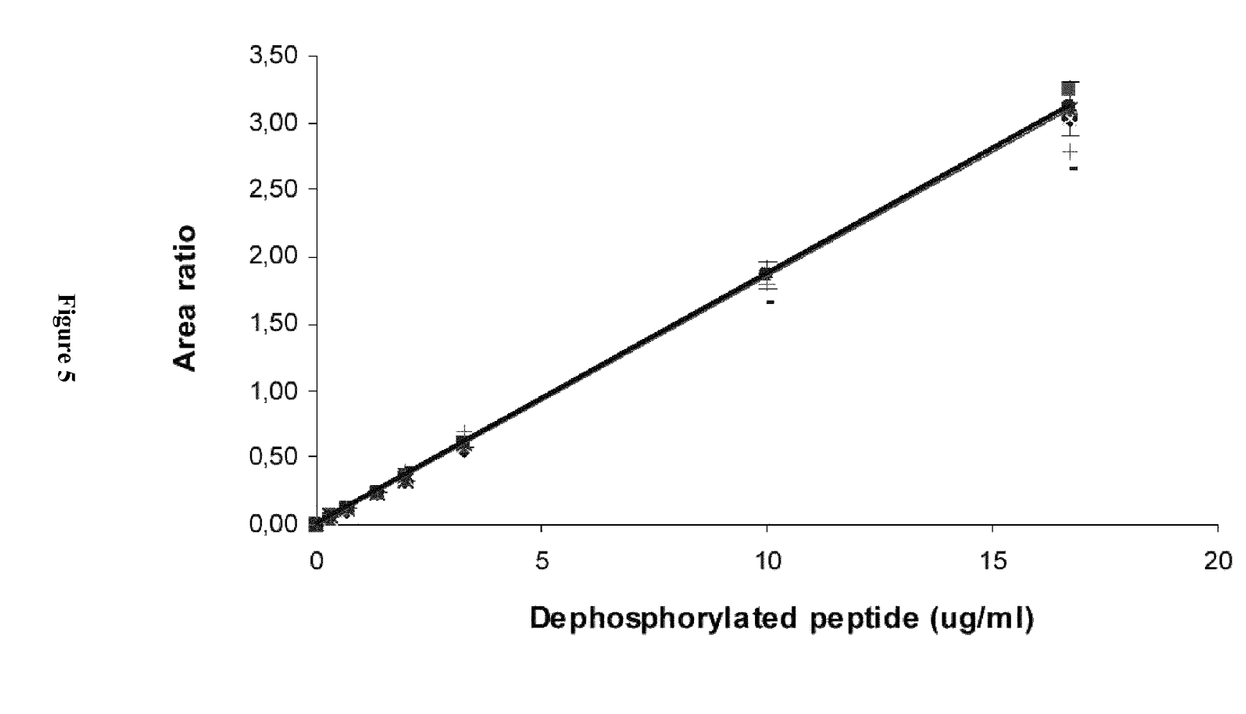
FIG. 5: Reproducibility for calibrations over a 12-day period.

The reproducibility of the assay was verified on 7 separate calibrations run over a period of 12 days as shown in FIG. 5. Each individual calibration had an $R^2$ of 0.9966 or greater. The mean regression equation for the 7 calibrations, where regression coefficient are expressed as mean (SD), was as follows: y=[0.1863 (0.055)]x−[0.0007 (0.00421)].

The precision of the assay was examined in PBMC protein extracts with known calcineurin activities ranging from 90 to 500 pmol/mg/min. Maximum intraassay and interassay variability was 11.5% and 16%, respectively (Table 2).

TABLE 2

Imprecision data for calcineurin activity measured in PBMC protein extracts

| sample name | mean measured pmol/mg/min | CV, % |
|---|---|---|
| Intraassay | | |
| 1 | 92 | 6.6 |
| 2 | 232 | 4.6 |
| 3 | 333 | 10.6 |
| 4 | 132 | 8.6 |
| 5 | 221 | 11.5 |
| 6 | 116 | 4.3 |
| Interassay | | |
| 7 | 337 | 10.5 |
| 8 | 91 | 8.7 |
| 9 | 160 | 11.5 |
| 10 | 375 | 8.0 |
| 11 | 362 | 5.6 |
| 12 | 454 | 13.5 |
| 13 | 452 | 11.7 |
| 14 | 356 | 12.8 |
| 15 | 140 | 12.3 |
| 16 | 179 | 16.0 |

Results

None of the methods described above discussed the possibility of rephosphorylation of DP-RII peptide during the CN enzymatic reaction process by kinases present in the cellular extracts.

The inventors assessed the kinetics of calcineurin in the presence or not of 2 different kinase inhibitors: H89, an unspecific inhibitor and Rp-adenosine 3′,5′-cyclic monophosphorothioate, a specific inhibitor of PKA.

A first set of experiments was performed using 5 µg of PBMC cytosolic proteins issued from healthy volunteers. Cells were resuspended in a buffer containing 50 mM Tris, pH=7.0, 0.1 mM EGTA, 0.05 mM dithiothreitol, 0.1% Tween 20, 0.3 mg/mL albumin, 1 mM $MnCl_2$, 1 mM $CaCl_2$ and protease inhibitors. Enzymatic reactions were processed at 37° C. in the 50 mM Tris buffer, pH=7.0, supplemented with 8 mg/L RII-P peptide, 0.03 units calmodulin, 500 nM okadaic acid and 1 mg/L stable isotope-RII peptide as an internal standard. The enzymatic reactions were stopped at the indicated time points (up to 120 min) and peptide amounts were quantified by LC-MS/MS.

Figure 1:
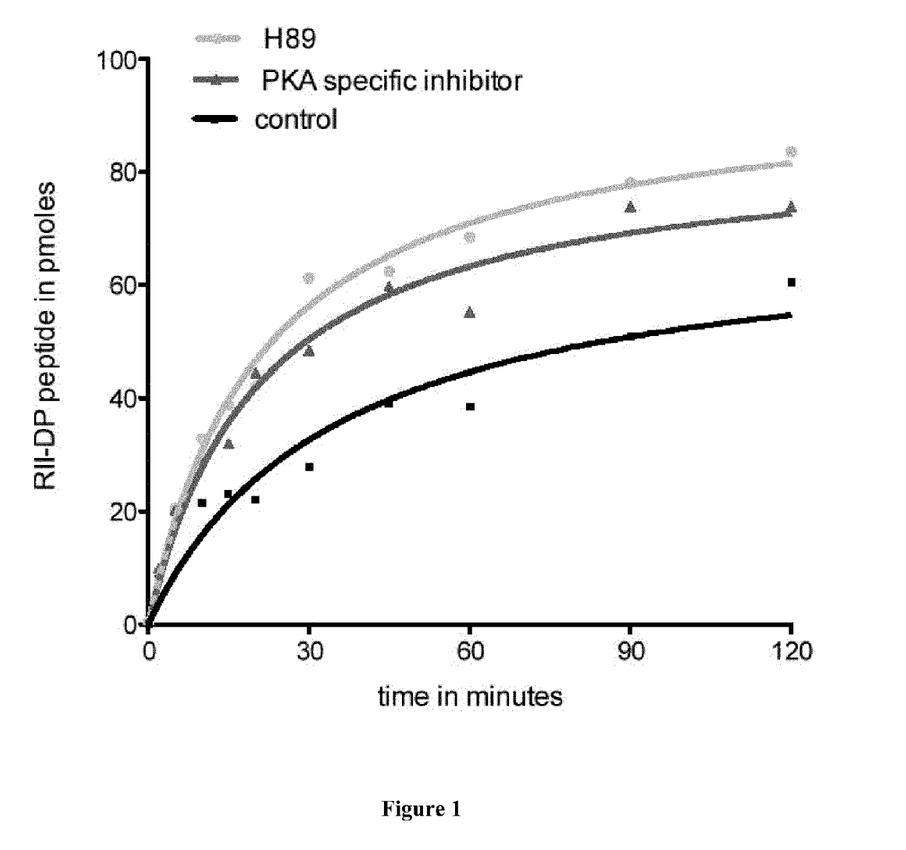
FIG. 1: Calcineurin kinetic experiments were performed in the presence or absence of two different kinase inhibitors. The production of DP-RII peptide was quantified using LC-MS/MS analysis.

As shown in FIG. 1, the production of DP-RII peptide was significantly higher in the presence of the kinase inhibitors (PKA specific inhibitor vs control, p=0.0008; H89 vs control, p=0.0007, ANOVA test). In addition, the inhibition obtained with H89 was significantly higher than that obtained with the PKA specific inhibitor (p=0.0163).

Figure 2:
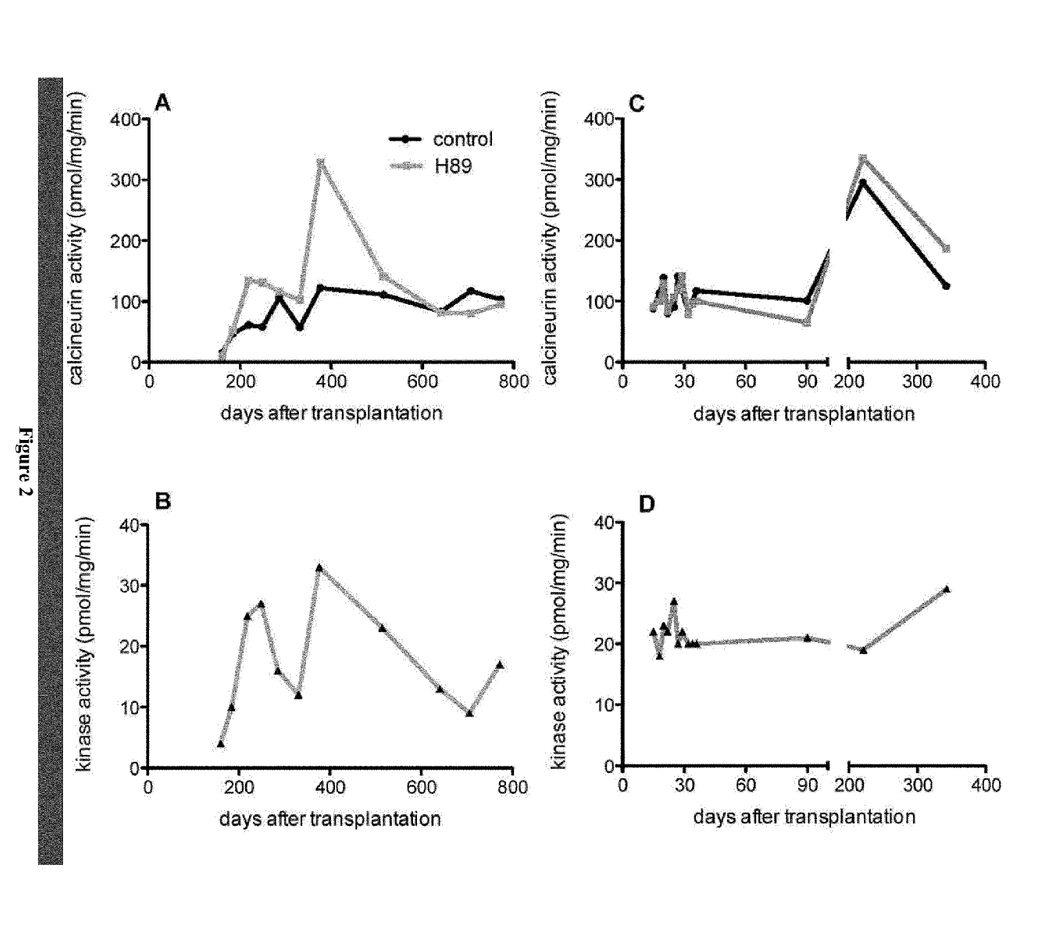
FIG. 2: Longitudinal follow-up of calcineurin and kinase activities in 2 transplant patients. A,B: Patient 1; C,D: Patient 2; A,C: Influence of H89 on calcineurin activity; B,D: kinase activity was quantified by means of LC-MS/MS.

To examine the importance of such an influence on a pharmacodynamic strategy for monitoring the extent of immunosuppression following transplantation, the inventors assayed PBMCs from transplant patients in the presence or absence of H89 kinase inhibitor, in a second set of experiments. As shown in FIG. 2, a strong variation in kinase activity was observed among patients and over time. Furthermore, the kinase activity was able to alter the measurement of CN activity, reflecting the relevance of our approach.

This finding demonstrates that the measurement of CN activity must be performed in the presence of a kinase inhibitor, in order to obtain a more specific measurement.

REFERENCES

Throughout this application, various references describe the state of the art to which this invention pertains. The disclosures of these references are hereby incorporated by reference into the present disclosure.

Donella-Deana A, Krinks M H, Ruzzene M, Klee C, Pinna L A. Dephosphorylation of phosphopeptides by calcineurin (protein phosphatase 2B). Eur J Biochem 1994, 219: 109-17.

Dumaz N, Marais R: Protein kinase A bloks Raf-1 activity by stimulating 14-3-3 binding and blocking Raf-1 interaction with Ras. J Biol Chem 2003; 278: 29819-23.

Enz A, Shapiro G, Chappuis A, Dattler A. Non radioactive assay for protein phosphatase 2B (calcineurin) activity using a partial sequence of the subunit of cAMP-dependent protein kinase as substrate. Anal Biochem 1994, 216: 147-53.

Freemerman A J, Turner A J, Birrer M J, Szabo E, Valerie K, Grant S: Role of c-jun in human myeloid leukaemia cell apoptosis induced by pharmacological inhibitors of protein kinase C. Mol Pharmacol 1996; 49: 788-95.

Fruman D A, Pai S Y, Klee C B, Burakoff S J, Bierer B E. Measurement of calcineurin phosphatase activity in cell extracts. Methods 1996, 9: 146-54.

Fukudo M, Yano I, Masuda S, Fukatsu S, Katsura T, Ogura Y, Oike F, Takada Y, Tanaka K, Inui K I. Pharmacodynamic analysis of tacrolimus and cyclosporine in living-donor liver transplant patients. Clin Pharmacol Therap 2005, 78: 168-81.

Gjertsen B T, Mellgren G, Otten A, Maronde E, Genieser H G, Jastorff B, Vintermyr O K, McKnight G S, Doskeland S O: Novel (Rp)-cAMPS analogs as tools for inhibition of camp-kinase in cell culture. J Biol Chem 1995; 270:20599-607.

Glass D B, Lundquist L J, Katz B M, Walsh D A: Protein kinase inhibitor-(6-22)-amide peptide analogs with standard and non-standard amino acid substitutions for phenylalanine 10. J Biol Chem 1989; 264: 14579-84.

Hidaka H, Inagaki M, Kawamoto S, Saaki Y: Isoquinolinesulfonamides, novel and potent inhibitors of cyclic nucleotide dependent protein kinase and protein kinase C. Biochemistry 1984; 23: 5036-41.

Ingebritsen T S, Cohen P. Protein phosphatases: Properties and role in cellular regulation. Science 1983, 221: 331-8.

Monaghan T K, MacKenzie C J, Plevin R, Ltz E M: PACAP-38 induces neuronal differentiation of human SH-SY5Y neuroblastoma cells via camp-mediated activation of ERK and p38 MAP kinases. J Neurochem 2008; 104: 74-88.

Murray A J: Pharmacological PKA inhibition: all may not be what it seems. Sci Signal 2008; 1(22):re4.

Ogreid D, Dostmann W, Genieser H G, Niemann P, Doskeland S O, Jastorff B: (Rp)- and (Sp)-8-piperidino-adenosine 3',5'-(cyclic)thiophosphates discriminate completely between site A and B of the regulatory subunits of camp-dependent protein kinase type I and II. Eur J Biochem 1994; 221: 1089-94.

Pallen C J, Wang J H. Calmodulin-stimulated dephosphorylation of p-nitrophenyl phosphate and free phosphotyrosine by calcineurin. J Biol Chem 1983, 258: 8550-3.

Qiu L B, Ding G R, Li K C, Wang X W, Zhou Y, Zhou Y C, Li Y R, Guo G Z: The role of protein kinase C in the opening of blood-brain barrier induced by electromagnetic pulse. Toxicology 2010; 273: 29-34.

Roberts B, Pohl J, Gooch J L. A fluorimetric method for determination of calcineurin activity. Cell Calcium 2008, 43: 515-9.

Rudolph J A, Pratt J, Mourya R, Steinbrecher K A, Cohen M B: Novel mechanism of cyclic AMP mediated extracellular signal regulated kinase activation in an intestinal cell line. Cell Signal 2007; 19: 1221-8.

Ruiz-Velasco V, Zhong J, Hume J R, Keef K D: Modulation of Ca2+ channels by cyclic nucleotide cross activation of opposing protein kinases in rabbit portal vein. Circ Res 1998; 82: 557-65.

Sanquer S, Schwarzinger M, Maury S, Yakouben K, Rafi H, Pautas C, Kuentz M, Barouki R, Cordonnier C. Calcineurin activity as a functional index of immunosuppression after allogeneic stem-cell transplantation. Transplantation 2004, 77: 854-8.

Sellar K J, van Rossum H H, Romijn F P, Smit N P, de Fijter J W, van Pelt J. Spectrophotometric assay for calcineurin activity in leukocytes isolated from human blood. Anal Biochem 2006, 358: 104-10.

Wang L Y, Salter M W, MacDonald J F: Regulation of kainite receptors by cAMPD-dependent protein kinase and phosphatases. Science 1991; 253: 1132-35.

Weisskopf M G, Castillo P E, Zalutsky R A, Nicoll R A: Mediation of hippocampal mossy fiber long-term potentiation by cyclic AMP. Science 1994; 265: 1878-82.

Yokozaki H, Tortora G, Pepe S, Maronde E, Genieser H G, Jastorff B, Cho-Chung Y S: Unhydrolyzable alalogues of adenosine 3':5'-monophosphate demonstrating growth inhibition and differentiation in human cancer cells. Cancer Res 1992; 52: 2504-8.

Zhang B, Zhang Y, Shacter E: Rac1 inhibits apoptosis in human lymphoma cells by stimulating Bad phosphorylation on Ser-75. Mol C.

The invention claimed is:

1. A method for measuring the activity of calcineurin in a biological sample comprising the steps of:
   providing a reaction mix comprising a substrate, at least one phosphatase inhibitor and at least one kinase inhibitor;
   incubating said biological sample with the reaction mix under conditions suitable for the activity of calcineurin;
   measuring the amount of dephosphorylated substrate.

2. A method according to claim 1, wherein the substrate is the phosphorylated peptide DLDVPIPGRFDRRVpSVAAE (SEQ ID NO:1).

3. A method according to claim 1, wherein the phosphatase inhibitor is okadaic acid.

4. A method according to claim 1, wherein the kinase inhibitor is H89.

5. A method according to claim 1, wherein the biological sample is a peripheral blood mononuclear blood cell (PBMC) sample.

6. A method according to claim 1, wherein the step of measuring the amount of dephosphorylated substrate is carried out by chromatography.

7. A method according to claim 6, wherein the step of measuring the amount of dephosphorylated substrate is carried out by liquid chromatography coupled with tandem mass spectrometry (LC-MS/MS).

8. A method for predicting the therapeutic outcome of a transplant patient comprising measuring the activity of calcineurin in a biological sample obtained from said patient according to claim 1.

9. A kit for measuring the activity of calcineurin in a biological sample comprising a calcineurine substrate, at least one phosphatase inhibitor and at least one kinase inhibitor.

* * * * *

SEQUENCE LISTING

```
<160> NUMBER OF SEQ ID NOS: 1

<210> SEQ ID NO 1
<211> LENGTH: 19
<212> TYPE: PRT
<213> ORGANISM: artificial
<220> FEATURE:
<223> OTHER INFORMATION: synthetic peptide
<220> FEATURE:
<221> NAME/KEY: PHOSPHORYLATION
<222> LOCATION: (15)..(15)

<400> SEQUENCE: 1

Asp Leu Asp Val Pro Ile Pro Gly Arg Phe Asp Arg Arg Val Ser Val
1               5                   10                  15

Ala Ala Glu
```